United States Patent [19]

Beshoory

[11] Patent Number: 4,763,536
[45] Date of Patent: Aug. 16, 1988

[54] FURNACE TUBE

[76] Inventor: Joseph E. Beshoory, 10926 Sagebluff, Houston, Tex. 77089

[21] Appl. No.: 841,431

[22] Filed: Mar. 19, 1986

[51] Int. Cl.$^4$ ............................................. G01N 25/00
[52] U.S. Cl. ..................................... 73/865.6; 374/14
[58] Field of Search .................. 73/19, 864.73, 863.81, 73/23, 865.6; 374/14

[56] References Cited

U.S. PATENT DOCUMENTS

| | | | |
|---|---|---|---|
| 3,373,598 | 3/1968 | Johnson et al. | 374/14 |
| 3,469,455 | 9/1969 | Iwata | 374/14 |
| 3,797,299 | 3/1974 | Nelson et al. | 73/19 |
| 3,902,354 | 9/1975 | Harlan et al. | 374/14 |
| 4,134,289 | 1/1979 | Bohl et al. | 73/23 |
| 4,346,583 | 8/1982 | Hoogstaat | 73/19 |

*Primary Examiner*—Stewart J. Levy
*Assistant Examiner*—Hezron E. Williams
*Attorney, Agent, or Firm*—Robert W. B. Dickerson

[57] ABSTRACT

An improved furnace tube, for use in a thermobalance, including an inner tube secured to an outer tube, said outer tube including (1) an inlet in communication with a coiled passageway which terminates in a diffuser, and (2) an outlet; said inner tube including passageways through an end thereof for accommodating both a beam and thermocouple means; and coupling means for joining together said inner and outer tubes as well as linking said tubes, collectively to a balance housing.

4 Claims, 1 Drawing Sheet

FURNACE TUBE

BACKGROUND OF THE INVENTION

Thermobalances have been developed to study, among many purposes, the reaction of gases with other substances. They are used in conjunction with questions of product stability and characterization. Such devices previously developed include a DUPONT THERMALGRAVIMETRIC ANALYZER (TGA) model 951. It has become highly desirable to improve the prior art so as to permit utilization in environments containing corrosive gas. It is to the satisfying of this need that Applicant's invention is directed.

SUMMARY OF THE INVENTION

Applicant's furnace tube may be secured to the balance housing of a thermobalance. The invention comprises first and second concentric tubes, the inner tube having passageways for a balance beam, and a sample thermocouple. Said beam would be intended to carry, at one end, the sample pan. The outer tube includes a treat, or reaction, fluid, ie, gas (or steam) inlet and a combined fluid, ie, gas outlet. Said inlet is linked by a coiled tube, forming a tortuous or spiral path, to a diffuser which is proximate to the sample pan. An inert purge gas enters the inner tube from the thermobalance balance housing and drives the treat, or reaction, gas, along with any reaction products or contaminants, out the outlet.

DESCRIPTION OF A PREFERRED EMBODIMENT

Figure 1:
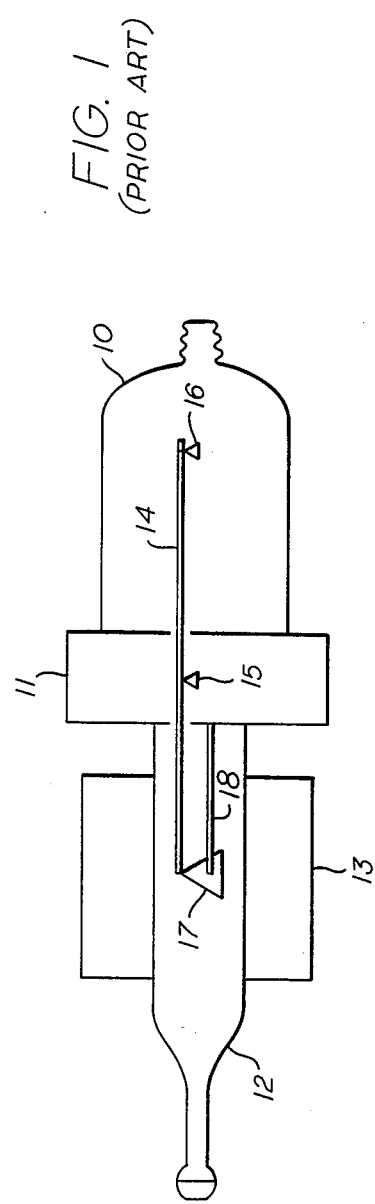
FIG. 1 is somewhat schematic elevation of the prior art.

FIG. 1 illustrates a prior art thermobalance. Such a device generally includes a bell jar 10 depending from one side of a balance housing 11. Depending from the other side of said housing is furnace tube 12, which extends through furnace 13. Quartz beam 14 is shown positioned on fulcrum 15, and extends within both the bell jar and the furnace tube. At opposite ends of beam 14, a counterweight 16 and sample pan 17 are suspended. A sample thermocouple 18 leads from the sample pan to electronics (not shown) positioned within the balance housing, or related structure, for performing known gravimetric measurement. Treat, or reaction fluid, ie, gas, would flow, from right to left, through the balance housing, across the sample provided the sample pan, and out the furnace tube to exhaust or for other analysis. Such arrangement does not adequately permit use of corrosive treat or reaction gas. A least one proposed improvement contemplated inner and outer furnace tubes. Treat gas, used therewith, would flow through the inner tube, across the sample in the sample pan and exit through a baffle to enter the outer tube. On such entry, such treat gas would encounter a purge fluid, ie, nitrogen pruge, entering said outer tube from the balance housing. The mixed gases would then course the annulus between said inner and outer furnace tubes to exit the outer tube.

Figure 2:
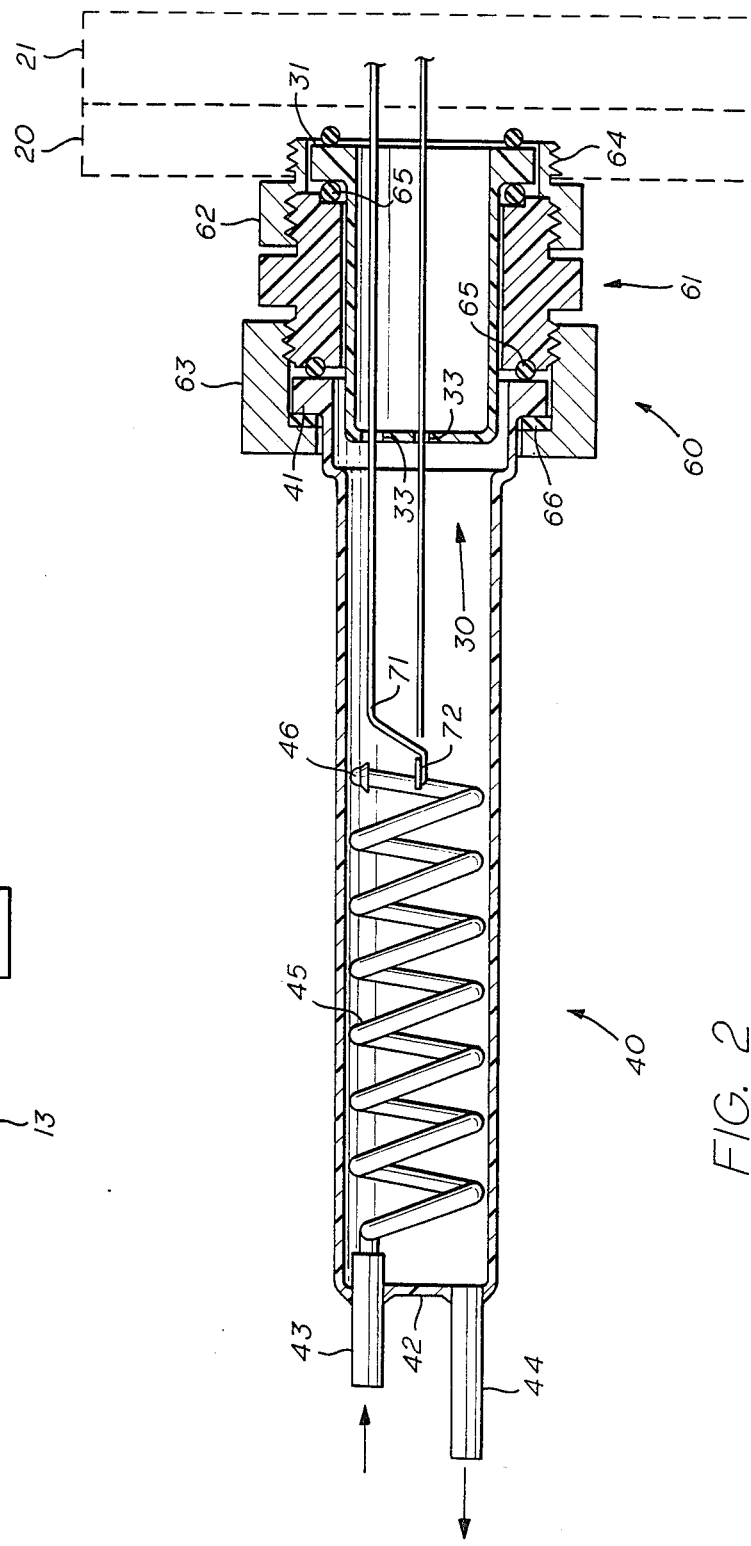
FIG. 2 is a somewhat schematic, vertical section through the furnace tube of this invention.

Consider now the improvement of FIG. 2. The phantom lines may be taken to represent a balance housing 20, including any necessary electronics, to perform gravimetric measurements in a known fashion, and a bell jar 21, or other receptacle for receiving a balance end. The furnace tube assembly of this invention includes inner tube 30, outer tube 40, and interlocking nut assembly 60. Both tubes would be fabricated of quartz glass, or other inert material.

Cup-shaped inner tube 30, includes annular lip 31. At the web end of said tube 30, at least a pair of perforations or openings 33 extend therethrough. Other tube 40 also includes an annular lip 41 around its slightly enlarged, open end. At its closed end web 42, gas inlet 43 and gas outlet 44 extend therethrough. Inlet tube 43 includes a coiled portion 45, terminating in a diffuser, shown schematically at 46. Such coiled portion causes the treat or sampled gas to course a spiral or tortuous path to diffuser 46, enhancing its heating.

Nut assembly 60 includes an exteriorly threaded, central nut portion 61, constructed of a corrosion-resistant substance, such as TEFLON. Interiorly threaded, inner and outer fasteners 62 and 63, the former having an exteriorly threaded, depending stem 64, for engagement with interior threads provided on balance housing 20, secure the inner and outer tubes' lips together, as well as permit securing the furnace tube assembly to the balance housing. Said fasteners 62, 63 may be fabricated of metal. O-rings 65, and annular bearing 66 sturdily prevent leakage of gases from the furnace tube assembly interior, and prevent corrosive treat or reaction gas from contacting the metal fasteners.

In operation, the inner tube 30 would be properly secured to the balance housing, by fastener 62. Alignment sould permit entry of one end of a sample beam 71, through an aperture 33. The beam would have its fulcrum within said balance housing. Pan 72 would be suspended from said one end of said beam. A thermocouple assembly (not shown) my extend through another aperture 33, to said pan. The pan would then be loaded with a sample. The sample may be, by way of example only, hydrocarbon material or organic chemicals. At this time, such balance beam end, sample pan, and thermocouple would be inserted within the outer tube 40, and said outer tube secured to inner tube 30, by outer lock washer 63. Treat or reaction gas would enter inlet 43 and be pre-heated on passing through coil portion 45 (said outer tube portion being positioned within a furnace, or the like, not shown) to exit through diffuser 46 to contact the sample in pan 72. Such treat gas may be a corrosive gas such as sulfur dioxide, hydrogen sulfide, ammonia, or any such gas wherein the effect of thermal decomposition of the sample is being studied. Said diffuser should be of porous material, such as quartz. The diffuser's presence allows treatment of the sample without the high velocity treat gas blowing sample from the pan or disrupting the balance beam function.

Any inert gas provided, such as nitrogen, acting as a purge gas, would enter housing 20, or bell jar 21, pass through inner tube 30, pass through one or more apertures 33, into outer tube 40, and expel the treat gas, along with any volatiles through exit 44. The gravimetric measuring instrumentation (not shown and not a part of this invention) within balance housing 20, may determine weight change of the sample, temperature, etc. The product exiting through 44 may be exhausted or have other analysis performed, such also not forming a part of this invention.

Although only a single embodiment has been described, it should be obvious that numerous modifications would be possible by one skilled in the art without departing from the spirit of the invention, the scope of which is limited only by the following claims.

What is claimed is:

1. A furnace tube assembly, comprising:

an inner tube and an outer tube;

said inner tube being open at one end and including means comprising at least one passageway means through its other end for permitting a first fluid to pass therethrough into said outer tube;

said outer tube comprising a second fluid inlet, a combined fluid outlet, second fluid diffuser means, and means for causing said second fluid to follow a tortuous path intermediate said second fluid inlet and said diffuser; and connector means for securing together said inner and outer tubes, said connector means comprises a nut fabricated of material resistant to corrosion, and further comprises at leat one adjustable fastener means fabricated of material less resistant to corrosion than said material comprising said nut, said assembly further including means to prevent exposure of said fastener means to said second fluid.

2. A furnace tube assembly for use in a balance mechanism, said assembly including:

first and second communicating tubes fabricated of a material resistant to corrosion;

said first tube including passageway means passing a 1st fluid therethrough into said second tube;

said second tube including 2nd fluid inlet means, 2nd fluid diffuser means, combined fluid outlet means, and means for causing said 2nd fluid to follow a tortuous path intermediate said 2nd fluid inlet and said diffuser;

connector means for joining said tubes, said connector means comprised of a nut resistant to corrosion, and of fastener means less resistant to corrosion than said nut, said assembly further including means for impairing contact between said 2nd fluid and said fastener means.

3. A furnace tube assembly for use in a balance mechanism, said assembly including:

first and second communicating tubes fabricated of a material resistant to corrosion;

said first tube including passageway means passing a 1st fluid therethrough into said second tube;

said second tube including 2nd fluid inlet means, 2nd fluid diffuser means, combined fluid outlet means, and means for causing said 2nd fluid to follow a tortuous path intermediate said 2nd fluid inlet and said diffuser;

connector means for joining said tubes;

said first tube passageway means includes aperture means through one end of said tube for permitting passage therethrough of said 1st fluid.

4. The assembly of claim 3, wherein said first tube passageway means also includes balance beam accommodating means.

* * * * *